(12) United States Patent  (10) Patent No.: US 8,222,418 B2
Hannam et al.  (45) Date of Patent: Jul. 17, 2012

(54) PIPERIDINES AND RELATED COMPOUNDS FOR THE TREATMENT OF DEMENTIA

(75) Inventors: Joanne Clare Hannam, Canterbury (GB); Sascha Hartmann, Braintree (GB); Andrew Madin, Cambridge (GB); Mark Peter Ridgill, Dover (GB)

(73) Assignee: Merck Sharp + Dohme Corp., Rahway, NJ (US)

( * ) Notice: Subject to any disclaimer, the term of this patent is extended or adjusted under 35 U.S.C. 154(b) by 766 days.

(21) Appl. No.: 12/294,303

(22) PCT Filed: Mar. 27, 2007

(86) PCT No.: PCT/GB2007/050155
§ 371 (c)(1),
(2), (4) Date: Jan. 30, 2009

(87) PCT Pub. No.: WO2007/110667
PCT Pub. Date: Oct. 4, 2007

(65) Prior Publication Data
US 2009/0239905 A1   Sep. 24, 2009

(30) Foreign Application Priority Data

Mar. 28, 2006 (GB) .................. 0606015.6

(51) Int. Cl.
*C07D 211/68* (2006.01)
*C07D 405/00* (2006.01)
(52) U.S. Cl. ....................... 546/194; 546/214
(58) Field of Classification Search .......... 546/194, 546/214
See application file for complete search history.

(56) References Cited

FOREIGN PATENT DOCUMENTS
WO   2006/043064 A1   4/2006

OTHER PUBLICATIONS

West, Solid State Chemistry and Its Applications, John Wiley & Sons, 1984.*
Dorwald F. A. (Side Reactions in Organic Synthesis, 2005, Wiley: VCH, Weinheim p. IX of Preface pp. 1-15.*
Venkatesh et al., Role of the Development Scientist in Compound Lead Selection and Optimization J. Pharm. Sci. 89, 145-54 (2000).*

* cited by examiner

*Primary Examiner* — Nizal Chandrakumar
(74) *Attorney, Agent, or Firm* — Susan L. Hess; Raynard Yuro; Gerard M Devlin

(57) ABSTRACT

Compounds of formula I: modulate the action of gamma secretase, and hence find use in treatment of Alzheimer's disease and related conditions.

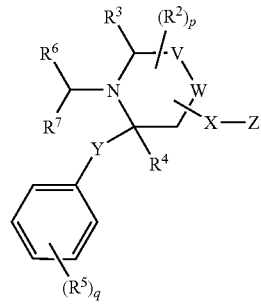

(I)

6 Claims, No Drawings

PIPERIDINES AND RELATED COMPOUNDS FOR THE TREATMENT OF DEMENTIA

RELATED APPLICATION DATA

This is a National filing under 35 U.S.C. 371 of PCT/GB2007/050155, filed Mar. 27, 2007, which claims priority under 35 U.S.C. 119(a) and 365(b) to GB0606015.6, filed Mar. 28, 2006.

This invention relates to compounds for use in therapeutic treatment of the human body. In particular, it provides carboxy-functional 1,2-disubstituted piperidines and related compounds useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS,* 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science,* 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature,* 423 (2003), 435-9).

Other proposed methods of treatment include administering a compound which blocks the aggregation of Aβ, and administering an antibody which selectively binds to Aβ.

Another proposed treatment is that of modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience,* 22 (2002), 226-54). US 2002/0015941 teaches that agents which potentiate capacitative calcium entry activity can lower Aβ(1-42).

It has now been found that certain carboxy-functional 1,2-disubstituted piperidines and related compounds have the desirable property of selectively inhibiting production of Aβ(1-42).

According to the present invention there is provided a compound of formula I:

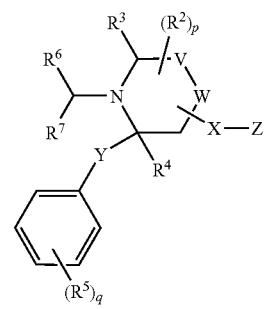

or a pharmaceutically acceptable salt or hydrate thereof; wherein:

p is 0 or 1;

q is 0, 1, 2 or 3;

V represents a bond or a carbon atom whose remaining valencies are satisfied via bonding to H, R$^2$ or X—Z or to any combination thereof;

W represents a nitrogen atom or a carbon atom whose remaining valencies are satisfied via bonding to H, R$^2$ or X—Z or to any combination thereof, provided that when W represents a nitrogen atom, V represents a carbon atom and the moiety X—Z is attached to W;

X represents a bond or C(R$^1$)$_2$ or CH$_2$C(R$^1$)$_2$, provided that when W represents N, X does not represent a bond;

Y represents a bond or CH$_2$ or CH$_2$CH$_2$;

Z represents CO$_2$H or a tetrazole ring;

each R$^1$ independently represents H or a non-aromatic hydrocarbon group of up to 6 carbon atoms; or the two R$^1$ groups complete a C$_{3-6}$alicyclic group;

R$^2$ represents a non-aromatic hydrocarbon group of up to 6 carbon atoms;

R$^3$ and R$^4$ each represents H, or when V and W each represents a carbon atom, R$^3$ and R$^4$ may together represent a CH$_2$CH$_2$ bridge;

each R$^5$ independently represents halogen, C$_{1-6}$alkyl bearing 0-3 fluorine substituents, C$_{1-6}$alkoxy bearing 0-3 fluorine substituents, or C$_{2-6}$alkenyl; and R$^6$ represents Het-A- where A represents a bond, CH$_2$ or 1,4-phenylene and Het represents a heterocyclic ring system of up to 10 ring atoms which optionally bears up to 3 substituents selected from halogen, C$_{1-4}$alkyl, CF$_3$, C$_{1-4}$alkoxy and C$_{1-4}$alkoxycarbonyl or which optionally bears a phenyl substituent which itself is optionally substituted with halogen, $C_{1-4}$alkyl, $C_{1-4}$alkoxy or $C_{1-4}$alkoxycarbonyl; and $R^7$ represents a hydrocarbon group of up to 10 carbon atoms which optionally bears a $CF_3$ substituent.

Where a variable occurs more than once in formula I, the identity taken by said variable at any particular occurrence is independent of the identity taken at any other occurrence.

As used herein, the expression "hydrocarbon group" refers to groups consisting solely of carbon and hydrogen atoms. Unless indicated otherwise, such groups may comprise linear, branched or cyclic structures, singly or in any combination consistent with the indicated maximum number of carbon atoms, which may be saturated or unsaturated, including aromatic.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl $C_{1-6}$alkyl", "$C_{2-6}$alkynyl" and "$C_{1-6}$alkoxy" are to be construed in an analogous manner.

The expression "$C_{3-6}$alicyclic" refers to cyclic non-aromatic hydrocarbon groups containing from 3 to 6 ring carbon atoms. Examples include cyclopropyl, cyclobutyl, cyclopentenyl, cyclopentyl and cyclohexyl.

The term "heterocyclic" refers to mono- or bicyclic ring systems in which at least one ring atom is selected from N, O and S. Unless indicated otherwise, the term includes both saturated and unsaturated systems, including aromatic systems. Heterocyclic groups may be bonded via a ring carbon or a ring nitrogen, unless otherwise indicated.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of the carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the isomeric forms encompassed by formula I, both optical and geometrical, fall within the scope of the invention, singly or as mixtures in any proportion. Thus the moieties:

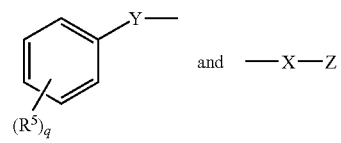

may be in a cis- or trans-configuration with respect to the ring completed by V—W. Furthermore, a given compound in the cis- or trans-configuration has two enantiomeric forms, both of which are within the scope of the invention, whether as single homochiral compounds or as racemic mixtures in any proportion. For the avoidance of any doubt, structural formulae such as (A) and (B):

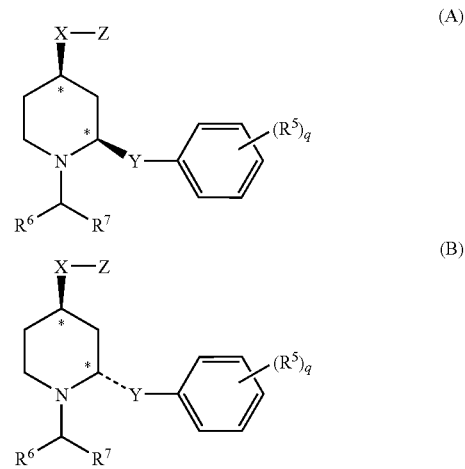

as used herein shall be taken to be definitive of the relative configurations of the carbon atoms marked with asterisks, but not their absolute configurations, unless expressly stated otherwise.

In formula I, V represents a bond or a carbon atom and W represents a nitrogen atom or a carbon atom, with the proviso that when W represents a nitrogen atom, V cannot be a bond and the moiety X—Z must be attached to W. Formula I therefore encompasses pyrrolidine, piperidine and piperazine derivatives, depending on the identities of V and W. In preferred embodiments, V represents a carbon atom, and hence completes a piperidine or piperazine ring. Most preferably, V and W both represent carbon atoms, and hence complete a piperidine ring. When one or both of V and W represents a carbon atom, the remaining valencies of said carbon atom(s) are satisfied via bonding to H, $R^2$ or X—Z, or to any combination thereof.

The moiety X—Z may be attached at any available ring position, including ring positions represented by V and W, but when W represents a nitrogen atom, X—Z must be attached to W. Preferably, X—Z is not attached at either of the positions adjacent to the nitrogen atom which is bonded to the moiety —$CHR^6R^7$. Thus, in the case of the preferred piperidine rings, X—Z is typically attached at the 3-, 4- or 5-position, preferably the 3- or 4-position, and most preferably at the 4-position. For the avoidance of doubt, the nitrogen atom of the piperidine ring shall be taken as the 1-position, and the carbon atom bonded to Y and $R^4$ as the 2-position.

Z represents $CO_2$ or a tetrazole ring, in particular, Z represents $CO_2H$ or 1,2,3,4-tetrazol-5-yl, but preferably represents $CO_2H$.

The group X represents a bond, $C(R^1)_2$ or $CH_2C(R^1)_2$, where each $R^1$ independently represents H or a non-aromatic hydrocarbon group of up to 6 carbon atoms; or the two $R^1$ groups complete a $C_{3-6}$alicyclic group (such as cyclopropyl, cyclobutyl, cyclopentenyl or cyclopentyl). Preferably, one $R^1$ group is H and the other is H or $C_{1-6}$alkyl such as methyl, ethyl, propyl or butyl. Particular identities for X include a bond, $CH_2$, $CH(CH_3)$, $CH_2CH_2$, cyclopentan-1,1-diyl and cyclopent-3-en-1,1-diyl, with the proviso that when W represents a nitrogen atom, X cannot be a bond. Preferably, X represents a bond or $CH_2$, and most preferably X represents $CH_2$.

Y represents a bond, $CH_2$ or $CH_2CH_2$, preferably a bond or $CH_2$, and most preferably a bond.

The group $R^2$ (when present) may be attached at any available position on the ring, including a carbon atom represented by V or W and including a carbon atom to which the moiety X—Z is attached. In one particular embodiment, p is 0 and $R^2$ is absent. In another particular embodiment, p is 1, V and W complete a piperidine ring and $R^2$ and the moiety X—Z are both attached at the 4-position thereof. In another particular embodiment, p is 1, V and W complete a piperidine ring, $R^2$ is attached at the 3-position and the moiety X—Z is attached at the 4-position. In another particular embodiment, p is 1, $R^3$ is H, V and W complete a piperidine ring, $R^2$ is attached at the 6-position and the moiety X—Z is attached at the 4-position. Typical identities for $R^2$ include $C_{1-6}$alkyl, such as methyl, ethyl or n-propyl, and $C_{2-6}$alkenyl, such as allyl.

$R^3$ and $R^4$ each represent H, or when V and W each represents a carbon atom, $R^3$ and $R^4$ may together represent —$CH_2CH_2$—, thereby completing a bridged bicyclic structure. When $R^3$ and $R^4$ together represent —$CH_2CH_2$—, p is preferably 0, and Y is preferably a bond. In a particular embodiment, $R^3$ and $R^4$ both represent H.

In formula I, q is preferably 1 or 2, most preferably 1. Each $R^5$ independently represents halogen (especially F), $C_{1-6}$alkyl bearing 0-3 fluorine substituents, $C_{1-6}$alkoxy bearing 0-3 fluorine substituents or $C_{2-6}$alkenyl. When one $R^5$ is present, it is very suitably (but not necessarily) attached in the 4-position. Typical identities for $(R^5)_q$ include 2-$CF_3$, 3-$CF_3$, 4-$CF_3$, 2,4-di($CF_3$), 2-F-4-$CF_3$, 4-$OCF_3$, 4-allyl, 4-n-propyl, 4-isopropyl and 4-tert-butyl. In one embodiment, $(R^5)_q$ represents 4-$CF_3$ or 4-n-propyl, in particular 4-$CF_3$.

$R^6$ represents Het-A where A represents a bond, $CH_2$ or 1,4-phenylene, and Het represents a heterocyclic system of up to 10 ring atoms which is optionally substituted as defined previously. Typically, Het represents a 5- or 6-membered heterocycle which optionally is fused to a second 5- or 6-membered ring. Said second 5- or 6-membered ring may be carbocyclic or heterocyclic, and when Het represents a group comprising a heterocyclic ring fused to a carbocyclic ring, attachment to the remainder of the molecule may be via either of these rings. Any ring comprised by the group represented by Het may be saturated or unsaturated, including aromatic. Examples of heterocyclic systems within the definition of Het include pyridine, quinoline, isoquinoline, furan, benzofuran, thiophene, benzothiophene, pyrazole, triazole, tetrahydropyran, tetrahydrothiopyran, piperidine and tetrahydrofuran. The group Het may be unsubstituted or substituted as defined previously. Preferred substituents (if present) include $CF_3$ $C_{1-4}$alkyl (especially methyl), $C_{1-4}$alkoxycarbonyl (such as t-butoxycarbonyl), phenyl and trifluoromethylphenyl.

When A represents 1,4-phenylene, Het typically represents a monocyclic system which does not bear a phenyl or substituted phenyl substituent.

Examples of groups represented by $R^6$ include: 3-pyridyl, 6-trifluoromethyl-3-pyridyl, 2-furyl, 5-(2-trifluoromethylphenyl)-2-furyl, 2-thienyl, 3-thienyl, benzothiophen-3-yl, 3-quinolinyl, benzofuran-2-yl, 6-quinolinyl, 1-phenyl-5-methylpyrazol-4-yl, furan-3-yl, 4-(pyridin-2-yl)phenyl, 4-(pyrazol-1-yl)phenyl, 4-(1,2,4-triazol-1-yl)phenyl, 4-(thiophen-2-yl)phenyl, tetrahydropyran-4-yl, (tetrahydrothiopyran-4-yl)methyl, 1-(t-butoxycarbonyl)piperidin-4-yl, (tetrahydropyran-4-yl)methyl, 4-(pyridin-4-yl)phenyl, 4-(pyridin-3-yl)phenyl and tetrahydrofuran-2-yl.

$R^7$ represents a hydrocarbon group of up to 10 carbon atoms optionally bearing a $CF_3$ substituent. Said hydrocarbon group may be fully saturated or may comprise one or more double or triple bonds or combinations thereof, and may include a phenyl ring. Typically, said hydrocarbon group contains up to 8 carbon atoms, e.g. up to 6 carbon atoms. Typical hydrocarbon groups include alkyl (in particular branched alkyl), alkenyl, alkynyl, cycloalkyl, cycloalkylalkyl, phenyl and phenylalkyl of up to 10 carbon atoms, e.g. up to 8 carbon atoms, and in particular up to 6 carbon atoms in total. In one embodiment $R^7$ represents an unsubstituted hydrocarbon group. Examples of unsubstituted hydrocarbon groups represented by $R^7$ include methyl, ethyl, n-propyl, isopropyl, n-butyl, t-butyl, 3-methylbutyl, 2-ethylbutyl, 4-methylpentyl, 3,3-dimethylbutyl, 3-methylbuten-1-yl, 3-methylbut-3-en-1-ynyl, 4-methylpent-1-ynyl, 3,3-dimethylbut-1-ynyl, cyclohexyl, phenyl, cyclopropylmethyl, cyclohexylethynyl, benzyl and 2-phenylethyl.

In an alternative embodiment, $R^7$ bears a $CF_3$ substituent. Examples of substituted hydrocarbon groups represented by $R^7$ include 2,2,2-trifluoroethyl, 3,3,3-trifluoropropyl, 4,4,4-trifluorobutyl, 1-methyl-3,3,3-trifluoropropyl, and 4-trifluoromethylphenyl.

A first subset of the compounds according to the invention consists of the compounds of formula II:

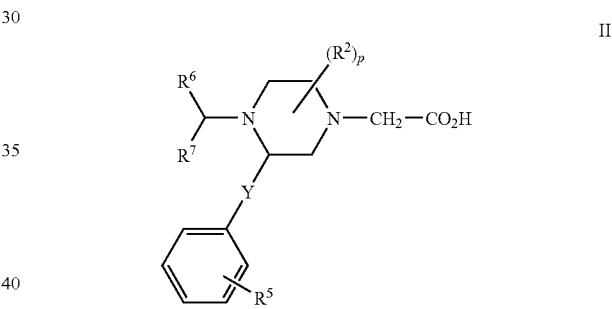

II and the pharmaceutically acceptable salts and hydrates thereof;

wherein p, $R^2$, $R^5$, $R^6$ and $R^7$ have the same definitions and preferred identities as before.

In a particular embodiment of this subset, p is 0 and Y is a bond.

A second subset of the compounds according to the invention consists of the compounds of formula III:

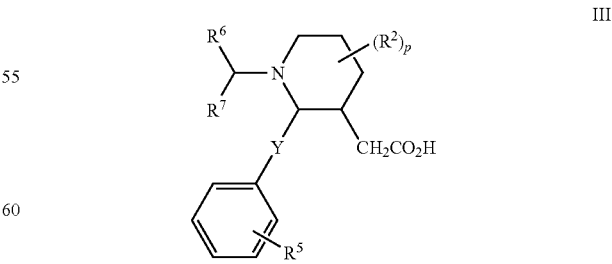

III and the pharmaceutically acceptable salts and hydrates thereof;

wherein p, $R^2$, Y, $R^5$, $R^6$ and $R^7$ have the same definitions and preferred identities as before.

Within this subset, Y is preferably a bond, and p is preferably O.

A third subset of the compounds according to the invention consists of the compounds of formula IV:

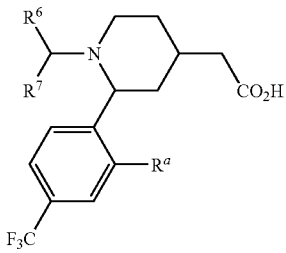

(IV)

and the pharmaceutically acceptable salts and hydrates thereof; wherein:

$R^a$ represents H, halogen or $CF_3$;

and $R^6$ and $R^7$ have the same definitions and preferred identities as before.

The substituted phenyl group attached to the 2-position of the piperidine ring and the $CH_2CO_2H$ group attached in the 4-position are advantageously (but not necessarily) in the cis-configuration with respect to the piperidine ring.

In a particular embodiment, $R^a$ represents H.

Specific compounds in accordance with the invention are described in the Examples section appended hereto.

The compounds of formula I in which Z is $CO_2H$ are typically obtained by hydrolysis of the corresponding esters (1):

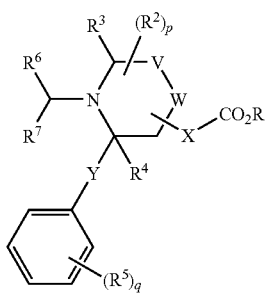

(1)

where R represents $C_{1-6}$alkyl such as methyl or ethyl and p, q, V, W, X, Y, $R^2$, $R^3$, $R^4$, $R^5$, $R^6$ and $R^7$ have the same meanings as before, e.g. by refluxing with LiOH in aqueous THF.

Corresponding compounds in which Z represents 1H-tetrazol-5-yl are obtainable by conversion of the esters (1) to the corresponding nitriles, followed by treatment with azidotrimethylsilane in refluxing toluene in the presence of tributyltin oxide. The conversion to the nitrile may be carried out by adding trimethylaluminum to a suspension of ammonium chloride in toluene, then adding the ester (1), refluxing the mixture, and treating with solid potassium sodium tartrate.

Compounds (1) may be obtained by reaction of compounds (2) with $R^6R^7CH$-L:

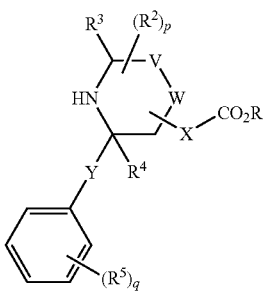

(2)

where L is a leaving group such as halide (especially bromide or iodide), tosylate, mesylate or triflate, and R, p, q, V, W, X, Y, $R^2$, $R^3$, $R^4$, $R^5$, $R^6$ and $R^7$ have the same meanings as before. Normal alkylating conditions may be employed, e.g. heating in DMF solution in the presence of base such as potassium carbonate.

Alternatively, compounds (2) may undergo reductive alkylation with precursors of the group $R^6R^7CH$— which contain an aldehyde or ketone functionality. In such cases, the compound (2) may be refluxed with $R^6$—CO—$R^7$ in toluene in the presence of an acid catalyst, with azeotropic removal of water, and the resulting adduct reduced using sodium triacetoxyborohydride. In a variant of this route, useful when $R^7$ is an alkyn-1-yl group, a compound (2) is reacted with $R^6$—CHO and $R^7$—H in the presence of gold(III) bromide, e.g. via microwave heating at 70° C. in water.

In another variant, the compound (2), $R^6$—CHO and benzotriazole are refluxed in toluene with azeotropic removal of water, and the resulting adduct reacted with $R^7$—Zn-Hal where Hal represents halide (preferably chloride) and $R^6$ and $R^7$ have the same meanings as before. The reaction is suitably carried out in an anhydrous aprotic solvent such as dichloromethane at reduced temperature, e.g. below 10° C.

Piperidines (2) in which V and W are both carbon atoms and $R^3$ and $R^4$ are H may be obtained by hydrogenation of the corresponding pyridines (3):

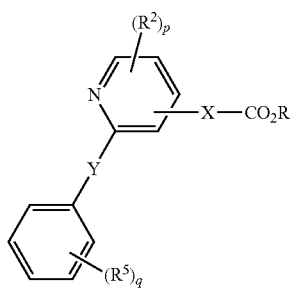

(3)

where R, p, q, X, Y, $R^2$ and $R^5$ have the same meanings as before, e.g. in methanolic HCl over a $PtO_2$ catalyst.

Pyridines (3) in which X is a bond and Y is a bond are obtainable by coupling of chloropyridines (4a) with arylboronic acids (5a):

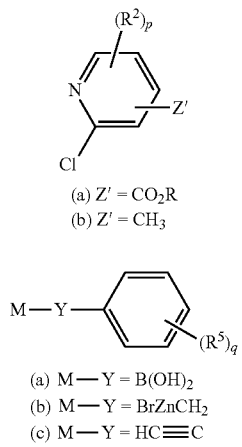

(a) Z′ = CO$_2$R
(b) Z′ = CH$_3$ (a) M—Y = B(OH)$_2$
(b) M—Y = BrZnCH$_2$
(c) M—Y = HC≡C where R, p, q, R$^2$ and R$^5$ have the same meanings as before. The reaction takes place under standard Suzuki coupling conditions, e.g. in aqueous dimethoxyethane in the presence of sodium carbonate and Pd(PPh$_3$)$_4$.

Pyridines (3) in which X is a bond and Y is CH$_2$ are obtainable by coupling of chloropyridines (4a) with benzylzinc derivatives (5b). The reaction may be carried out at 0° C. to ambient temperature in THF in the presence of a nickel catalyst such as (Ph$_3$P)$_2$NiCl$_2$.

Pyridines (3) in which X is a bond and Y is CH$_2$CH$_2$ are obtainable by coupling of chloropyridines (4a) with alkynes (5c) followed by hydrogenation. The coupling may be carried out in the presence of CuI and a Pd(0) catalyst such as Pd(Ph$_3$)$_4$, e.g. in a mixture of dioxan and triethylamine with microwave heating. The hydrogenation takes place under similar conditions to the conversion of pyridines (3) to piperidines (2), and indeed is preferably combined with that process.

Pyridines (3) in which X is CH$_2$ may be obtained by elaboration of chloropyridines (4b) with (5a), (5b) or (5c) as described above, then treating the product with CO(OR)$_2$ in the presence of strong base such as lithium diisopropylamide, where R has the same meaning as before. Alternatively, the chloropyridines (4b) may be treated with CO(OR)$_2$ prior to the reaction with (5a), (5b) or (5c).

Piperidines of formula (2) in which V and W are both carbon atoms and R$^3$ and R$^4$ are H, X is a bond, p is 1 and R$^2$ is attached to the same ring position as the CO$_2$R group are obtained by alkylation of the corresponding compounds in which p is 0 with R$^2$-L, where L has the same meaning as before. The reaction may be carried out in THF solution in the presence of strong base such as lithium hexamethyldisilazide (HMDS). During this procedure, it is preferable to protect the 1-position of the piperidine ring, e.g. as the BOC derivative.

An alternative route to esters (1) in which V and W are both carbon atoms and R$^3$ and R$^4$ are H, p is 0, X is CH$_2$ and the CH$_2$CO$_2$R group is attached to the 4-position involves condensation of piperidones (6) with (RO)$_2$P(O)CH$_2$CO$_2$R, followed by hydrogenation of the resulting olefin (7):

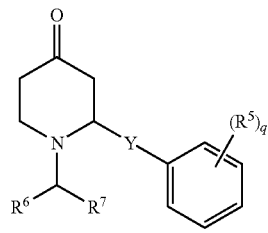

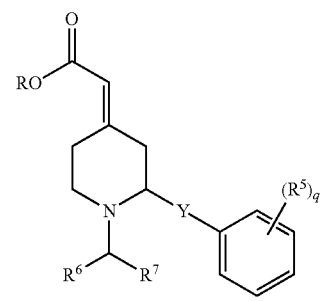

where R, Y, q, R$^5$, R$^6$ and R$^7$ have the same meanings as before. The condensation takes place in THF in the presence of NaH, while the hydrogenation may be carried out over a Pd/C catalyst in ethanol. Corresponding esters of formula (1) in which X is a bond may be obtained by treatment of ketones (6) with KHMDS and Tf$_2$NPh, then with CO and ROH in the presence of a Pd(II) catalyst, followed by hydrogenation of the resulting tetrahydropyridine derivative.

Ketones (6) are available by reduction of dihydropyridones (8):

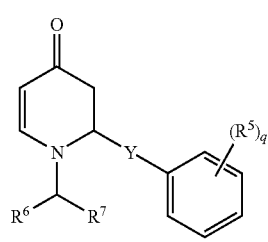

where Y, q, R$^5$, R$^6$ and R$^7$ have the same meanings as before. The reduction may be carried out using a borohydride reductant such as L-Selectride in THF at −78° C.

Compounds (8) are available by the Diels-Alder reaction between trans-1-methoxy-3-(trimethylsilyloxy)-1,3-butadiene and the imine formed from condensation of R$^6$R$^7$CH—NH$_2$ and an aldehyde (9):

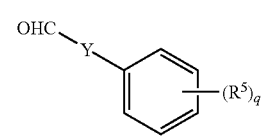

where Y, q, R$^5$, R$^6$ and R$^7$ have the same meanings as before. The cycloaddition may be carried out in acetonitrile at ambient temperature in the presence of In(III) inflate, followed by quenching with aqueous bicarbonate.

Alternatively, piperidones(6) may be obtained in a one-pot process by reacting the aforesaid imines with trimethyl[(1- methyleneprop-2-en-1-yl)oxy]silane (e.g. in dichloromethane at ambient temperature under an inert atmosphere), then adding tetrabutylammonium fluoride.

An alternative route to piperidines (2) in which V and W are both carbon atoms and $R^3$ and $R^4$ are H, p is 0, X is $CH_2$ and the $CH_2CO_2R$ group is attached to the 4-position involves elaboration of the dihydropyridones (10):

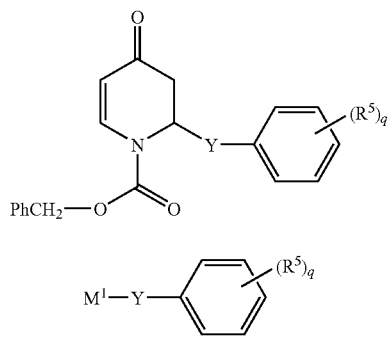

(10)

(11)

where Y, q and $R^5$ have the same meanings as before, in the manner described above for dihydropyridines (8), followed by removal of the benzyloxycarbonyl protecting group (e.g. by treatment with acid). Compounds (10) are available by a one-pot reaction of 4-methoxypyridine with benzyl chloroformate and organometallic derivatives (11), where $M^1$ is Li or Mg-halide, and Y, q and $R^5$ have the same meanings as before. The reaction takes place at reduced temperature (e.g. −25° C.) in a solvent such as THF.

In the above-described routes involving dihydropyridines (8) or (10), Y is preferably a bond.

The above-described routes involving dihydropyridines (8) or (10) may be adapted to provide products having an $R^2$ in the 3-position of the piperidine ring via alkylation of the compounds (8) or (10) with $R^2$-L, where $R^2$ and L have the same meanings as before. Said alkylation takes place under conventional conditions (e.g. in THF in the presence of lithium diisopropylamide).

Alternatively, the aforesaid routes may be adapted to provide products having an $R^2$ group in the 6-position of the piperidine ring via treatment of compounds (8) or (10) with $R^2$—Mg-halide in the presence of CuI, where $R^2$ has the same meaning as before. The reaction may be carried out in THF at reduced temperature (e.g. −78° C. to −10° C.).

In a further alternative, the aforesaid routes may be adapted to provide products in which the —$CH_2CO_2R$ group is attached at the 3-position of the piperidine ring via alkylation of compounds (8) or (10) with L-$CH_2CO_2R$, where L and R have the same meanings as before, followed by reduction of the keto group to $CH_2$. The alkylation takes place under conventional conditions, and reduction of the keto group is readily effected via treatment with 1,2-ethanedithiol to form the dithioketal, followed by treatment with Raney nickel.

An alternative route to piperidines of formula (1) in which V and W are both carbon atoms and $R^3$ and $R^4$ are both H, X is a bond, p is 0 and $CO_2R$ is attached to the 5-position involves cyclisation of dienes (12) followed by reduction of the resulting 1,2,3,6-tetrahydropyridine derivative:

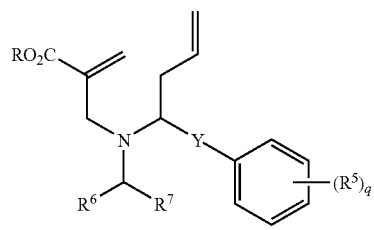

(12)

where R, Y, q, $R^5$, $R^6$ and $R^7$ have the same meanings as before. The cyclisation takes place in the presence of a Ru catalyst and the reduction may be effected by treatment with Mg in methanol. Dienes (12) are obtainable by alkylation of secondary amines (13) with the appropriate bromomethacrylate ester, and amines (13) are available by condensation of aldehydes (9) with $R^6R^7CH$—$NH_2$ and treatment of the product with allyltributylstannane:

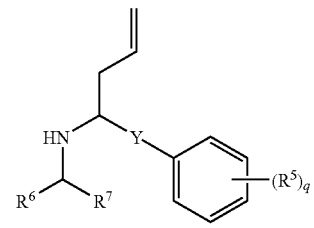

(13)

where Y, q, $R^5$, $R^6$ and $R^7$ have the same meanings as before.

Another route to piperidines of formula (1) in which V and W are both carbon atoms, p is 0, $R^3$ and $R^4$ are both H, X is a bond and $CO_2R$ is attached in the 4-position involves monodecarboxylation of bis-esters (14):

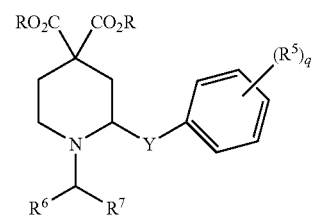

(14)

where R, Y, q, $R^5$, $R^6$ and $R^7$ have the same meanings as before. The reaction may be carried out by heating at about 160° C. with sodium chloride in DMSO. Subsequent reflux of the product with sodium methoxide in methanol causes epimerisation at the 4-position and enrichment with the cis-isomer at the expense of the trans-isomer. Bis-esters (14) are available from the reaction of amines $R^6R^7CH$—$NH_2$ with diketones (15):

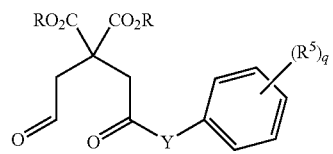

(15)

followed by reduction with sodium cyanoborohydride in a one-pot procedure, where R, Y, q, $R^5$, $R^6$ and $R^7$ have the same meanings as before. The first step may be carried out in dimethoxyethane in the presence of a tertiary amine and $TiCl_4$ at −78° C. with warming to ambient. The second step may be carried out by adding a methanolic solution of sodium cyanoborohydride to the reaction mixture at room temperature. Diketones (15) may be obtained by alkylation of the appropriate allylmalonate dialkyl ester with a compound of formula (16):

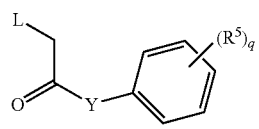

(16)

followed by ozonolysis of the allyl group, where L, R, Y, q and $R^5$ have the same meanings as before. The alkylation may be carried out in DMF in the presence of NaH (e.g. at ambient temperature). The ozonolysis may be effected by passing ozone-enriched oxygen through a dichloromethane solution of the substrate at −78° C., adding dimethyl sulfide, then stirring overnight at ambient temperature.

Piperidines of formula (2) in which $R^3$ and $R^4$ complete a —$CH_2CH_2$— bridge and Y is a bond may be obtained by elaboration of bicyclic ketones (17):

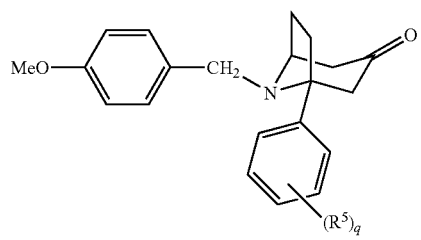

(17)

wherein q and $R^5$ have the same meanings as before, by the methods described above for the conversion of ketones (6) to esters (1), followed by removal of the protecting group 4-methoxybenzyl by hydrogenation.

The bicyclic ketones (17) are available by reaction of 4-methoxybenzylamine with acetonedicarboxylic acid, then treatment of the product in situ with a ketoaldehyde (18):

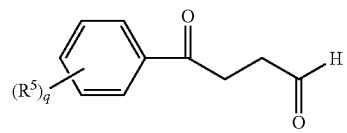

(18)

where $R^5$ and q have the same meanings as before.

A preferred route to piperazines of formula (1) in which V is a carbon atom and W is a nitrogen atom involves alkylation of compounds (19) with L-X'—$CO_2R$:

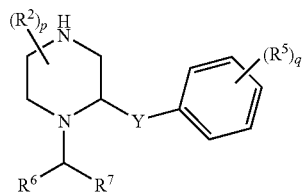

(19)

where X' is X that is other than a bond and all other variables are as defined previously. Compounds (19) are available from compounds (20):

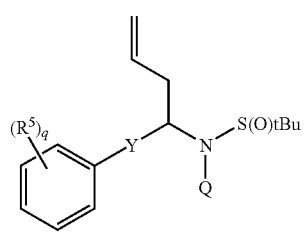

(20)

using the methods described previously for conversion of compounds (2) to compounds (1), followed by removal of the trityl group (e.g. by treatment with methanolic HCl). Compounds (20) are available via coupling of compounds (5a), (5b) or (5c) with the appropriate pyrazine derivatives in the manner described above for the synthesis of pyridines (3), followed by hydrogenation (as in the conversion of compounds (3) to compounds (2)) and tritylation by standard methods.

A preferred route to pyrrolidines of formula (1) in which V is a bond, p is 0 and X represents $CH_2$ involves the steps of (a) condensing an aldehyde (9) with t-butylsulphinamide and reacting the resulting imine with allylMgBr to provide the adduct (21a):

(21)

(a) Q = H
(b) Q = $CHR^6R^7$ (b) N-alkylation to provide compounds (21b) (e.g. by any of the methods described previously for converting (2) to (1));
(c) reaction with $CH_2$=CH—$CO_2R$ in the presence of a ruthenium catalyst (e.g. Zhan I), followed by treatment with methanolic HCl, to provide compounds (22a):

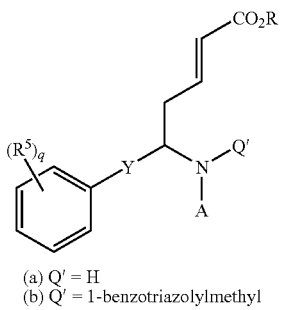

(22)

(a) Q' = H
(b) Q' = 1-benzotriazolylmethyl (d) reaction with 1-hydroxymethylbenzotriazole (e.g. in refluxing benzene with molecular sieves) to provide compounds (22b); and
(e) cyclisation by treatment with $SmI_2$ and t-butanol in THF at −78° C.

It will be readily apparent that several of the above-described routes are suitable for the synthesis of compounds of formula IV. Thus, in one preferred route to the ester precursors of compounds of formula IV, a piperidine of formula (2a), an aldehyde $R^6$—CHO and benzotriazole are refluxed in toluene with azeotropic removal of water, and the resulting adduct reacted with $R^7$—Zn-Hal

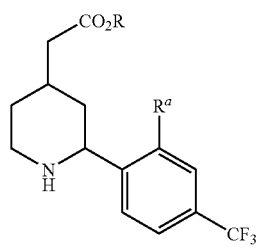

(2a)

where Hal represents halide (preferably chloride) and $R^a$, R, $R^6$ and $R^7$ have the same meanings as before. The reaction is suitably carried out in an anhydrous aprotic solvent such as dichloromethane at reduced temperature, e.g. below 10° C. Piperidines (2a) are available via coupling of pyridines (4b) with the appropriate boronic acid (5a) and further elaboration of the product as described previously. It will be readily apparent that the same result can be achieved by reacting a piperidine (2a) with an aldehyde $R^7$CHO and benzotriazole, and treating the resulting adduct with $R^6$—Zn-Hal. When the second step is carried out in a solvent comprising THF, a side-reaction may take place involving the THF, providing products in which $R^6$ represents 2-furyl.

In another preferred route to compounds of formula IV, a piperidine of formula (2a), an aldehyde $R^6$—CHO and a 1-alkyne are subjected to microwave heating in the presence of gold(III) bromide (e.g. at about 70° C.), providing compounds of formula IV in which $R^7$ is 1-alkynyl. If desired, the corresponding compounds in which $R^7$ is alkyl or alkenyl may be obtained by hydrogenation of the alkynyl derivatives (e.g. in ethyl acetate over a Pd/C catalyst).

In a third route to compounds of formula IV, the appropriate diketone of formula (15) (Y=a bond) is reacted with an amine of formula $R^6R^7CH$—$NH_2$ followed by treatment with sodium cyanoborohydride as described previously for the preparation of compounds (14). Thereafter, mono-decarboxylation (as described previously) and homologation (as described below) provide the compounds of formula IV.

Carboxylic acids of formula I in which X is a bond may be converted to the corresponding compounds in which X is $CH_2$ by standard methods of homologation, for example sequential treatment with oxalyl chloride; trimethylsilyldiazomethane and acetonitrile; ROH and silver benzoate; then hydrolysis of the resulting ester. Similar treatment of the corresponding compounds in which X is $CH_2$ provides the compounds in which X is $CH_2CH_2$. Esters of formula (1) in which X is $C(R^1)_2$ or $CH_2C(R^1)_2$ and at least one $R^1$ is other than H may be prepared by alkylation of the corresponding compounds in which each $R^1$ is H by standard methods.

Similarly, a given compound in accordance with formula I may be converted to a different compound in accordance with formula I by means of the standard techniques of bond formation or cleavage known to those skilled in the art of organic synthesis.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps. For example, racemic piperidine derivatives (2a) may be resolved via salt formation with L-mandelic acid.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3rd ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, American Family Physician, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al, Arch. Neurol, 56 (1999), 303-8.

Further information on the differential diagnosis of MCI is provided by Knopman et al, Mayo Clinic Proceedings, 78 (2003), 1290-1308. In a study of elderly subjects, Tuokko et al (Arch, Neurol., 60 (2003) 577-82) found that those exhibiting MCI at the outset had a three-fold increased risk of developing dementia within 5 years.

Grundman et al (J. Mol. Neurosci., 19 (2002), 23-28) report that lower baseline hippocampal volume in MCI patients is a prognostic indicator for subsequent AD. Similarly, Andreasen et al (Acta Neurol. Scand, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al, J. Psych. Res., 12 (1975), 196-198, Anthony et al, Psychological Med., 12 (1982), 397-408; Cockrell et al, Psychopharmacology, 24 (1988), 689-692; Crum et al., J. Am. Med. Assoc'n. 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., Am. J. Psychiatry, 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671.), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Within this embodiment, the amyloid modifier is advantageously a γ-secretase inhibitor, preferred examples of which include a compound of formula XI:

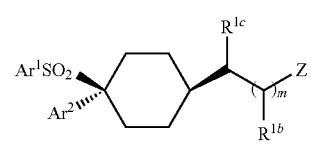

wherein m, Z, $R^{1b}$, $R^{1c}$, $Ar^1$ and $Ar^2$ are as defined in WO 03/018543;

or a pharmaceutically acceptable salt thereof.

Such compounds may be prepared as described in WO 03/018543. Preferred examples include those defined by formula XIa:

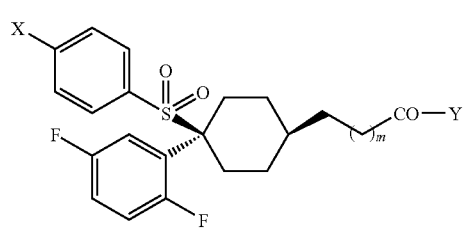

and the pharmaceutically acceptable salts thereof, wherein m is 0 or 1, X is Cl or $CF_3$, and Y is OH, $OC_{1-6}$alkyl, $NH_2$ or $NHC_{1-6}$alkyl. Particular examples include those in which m is 1 and Y is OH (or the sodium salts thereof), and those in which m is 0 and Y is $NH_2$ or $NHC_{1-6}$alkyl.

Another preferred class of γ-secretase inhibitors for use in this embodiment of the invention is that defined by formula XII:

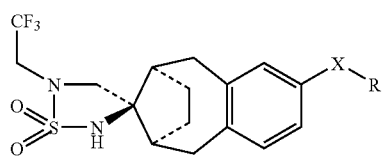

XII wherein X and R are as defined in WO 03/093252;
or a pharmaceutically acceptable salt thereof.

X is very aptly 5-substituted-thiazol-2-yl, 5-substituted-4-methylthiazol-2-yl, 5-substituted-1-methylpyrazol-3-yl, 1-substituted-imidazol-4-yl or 1-substituted-1,2,4-triazol-3-yl. Preferably, R represents optionally-substituted phenyl or heteroaryl such as phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Particularly preferred identities of R—X— include 5-(4-fluorophenyl)-1-methylpyrazol-3-yl, 5-(4-chlorophenyl)-1-methylpyrazol-3-yl and 1-(4-fluorophenyl)imidazol-4-yl. Such compounds may be prepared by methods disclosed in WO 03/093252.

Alternatively, the amyloid modifier may be a compound which inhibits the aggregation of Aβ. Suitable examples include chelating agents such as clioquinol (Gouras and Beal, Neuron, 30 (2001), 641-2) and the compounds disclosed in WO 99/16741, in particular that known as DP-109 (Kalendarev et al, J. Pharm. Biomed. Anal., 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 and the compound known as Alzhemed™ (Neurochem); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

In a further aspect, the invention provides the combination of a compound of formula I or a pharmaceutically acceptable salt thereof and a compound of formula XI(a) or a pharmaceutically acceptable salt thereof for use in treatment or prevention of a disease associated with deposition of β-amyloid in the brain. Said use may involve the simultaneous or separate administration of the respective compounds to a patient in need of such treatment or prevention.

In a further aspect, the invention provides a pharmaceutical composition comprising, in a pharmaceutically acceptable carrier, a compound of formula I or a pharmaceutically acceptable salt thereof and a compound of formula XI(a) or a pharmaceutically acceptable salt thereof. Preferably, the pharmaceutical composition is in a unit dose form suitable for oral administration, such as a tablet or a capsule.

EXAMPLES

The ability of the compounds of Formula I to selectively inhibit production of Aβ(1-42) was determined using the following assay:
Cell-Based γ-Secretase Assay Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 10 µl and 50 µl media were transferred into a fresh Costar round-bottom 96-well plate for detection of Aβ(40) and Aβ(42) peptides, respectively. 40 µl Origen buffer (PBS, 2% BSA, 0.2% Tween-20) was added to the Aβ(40) wells followed by the addition of 25 µl the respective antibody premixes to the wells:

Aβ(40) premix: 1 µg/ml ruthenylated G2-10 antibody, 4 µg/ml
  biotinylated 4G8 antibody diluted in Origen buffer
Aβ(42) premix: 0.5 µg/ml ruthenylated G2-11 antibody, 4 µg/ml
  biotinylated 4G8 antibody diluted in Origen buffer
(Biotinylated 4G8 antibody supplied by Signet Pathology Ltd; G2-10 and G2-11 antibodies supplied by Chemicon)

After overnight incubation of the assay plates on a shaker at 4° C., the Origen M8 Analyser (Igen Inc.) was calibrated according to the manufacturer's instructions. 25 µl of streptavidin magnetic bead (Dynal) premix (400 µg/ml streptavidin beads/ml in Origen buffer) was added to the assay plates and incubated on a shaker for 15 minutes. 150 µl Origen buffer was added to each well and the plates were read on the Origen M8 Analyser according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 μl of 10×MTS/PES was added to the remaining 50 μl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for A (1-42) inhibition that were at least 2-fold lower than the corresponding $IC_{50}$ values for A (1-40) inhibition, typically at least 5-fold lower, and in the preferred cases at least 50-fold lower.

Intermediate 1

(±)-Methyl {2-[4-(trifluoromethyl)phenyl]piperidin-4-yl}acetate hydrochloride

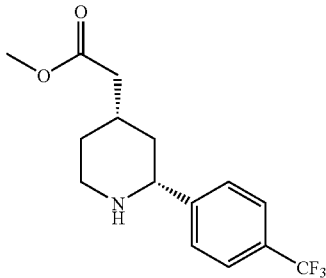

Step 1:
4-Methyl-2-[4-(trifluoromethyl)phenyl]pyridine

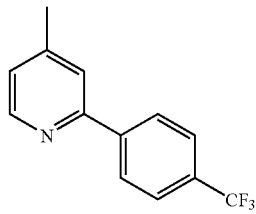

A mixture of 2-chloro-4-methylpyridine (1.9 ml, 21.6 mmol) and 4-(trifluoromethyl)benzeneboronic acid (5.0 g, 26 mmol) in DME (40 ml) and aqueous $Na_2CO_3$ (2M, 40 ml) was degassed (Firestone® valve ×3). Tetrakis(triphenylphosphine) palladium (0) (1.15 g, 11.0 mmol, 5 mol %) was added and following a further degassing (Firestone® valve ×3) the mixture was heated at reflux for 16 hours. The reaction was cooled to room temperature diluted with $H_2O$ (100 ml) and EtOAc (150 ml). The mixture was filtered through a Celite® pad, washing through with EtOAc. The phases were separated and the aqueous layer was extracted with EtOAc (200 ml). The combined extracts were washed with $H_2O$ (100 ml) and brine (×1), then dried ($MgSO_4$), filtered and evaporated. The residue was purified by chromatography on silica, eluting with 10% EtOAc/isohexane to give the ester (3.5 g, 68%) as a white solid. $^1$H NMR (360 MHz, $CDCl_3$) δ: 2.44 (3H, s), 7.13 (2H, d, J 5.0), 7.58 (1H, s), 7.72 (2H, d, J 8.2), 8.09 (2H, d, J 8.2), 8.57 (1H, d, J 5.0).

Step 2: Methyl {2-[4-(trifluoromethyl)phenyl]pyridin-4-yl}acetate

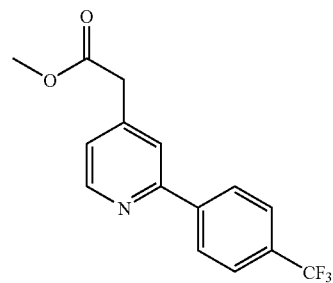

A solution of LDA (2M in THF/heptane/ethyl benzene, 44 ml, 88 mmol) was added dropwise to a stirred solution of 4-methyl-2-[4-(trifluoromethyl)phenyl]pyridine (10.5 g, 44 mmol) in dry THF (300 ml) under $N_2$, such that the internal temperature remained <−70° C. After 1 hour at this temperature, dimethyl carbonate (8.9 ml, 106 mmol) was added. After 30 minutes the cooling bath was removed. When the internal temperature had reached −20° C. the reaction was transferred to a cold bath at −10° C., and then allowed to warm slowly to 0° C. After 1 hour at 0° C. the reaction was quenched with aqueous $NH_4Cl$ (half saturated, 100 ml). The reaction mixture was concentrated in vacuo. The residue was diluted with $H_2O$ (200 ml) and extracted with EtOAc (2×200 ml). The combined extracts were washed with brine (×1), then dried ($MgSO_4$), filtered and evaporated. The residue was purified by chromatography on silica, eluting with 10-30% EtOAc/isohexane to give the ester (9.2 g, 71%) as a pale yellow liquid. $^1$H NMR (400 MHz, $CDCl_3$) δ: 3.72 (2H, s), 3.75 (3H, s), 7.24 (1H, dd, J 1.4, 5.0), 7.72 (3H, t, J 8.4), 8.11 (2H, d, J 8.2), 8.68 (1H, d, J 5.0).

Step 3: (±)-Methyl {2-[4-(trifluoromethyl)phenyl] piperidin-4-yl}acetate hydrochloride A mixture of methyl {2-[4-(trifluoromethyl)phenyl]pyridin-4-yl}acetate (6.2 g, 21 mmol), $PtO_2$ (200 mg, 0.9 mmol) and HCl solution (4N in dioxane, 5.8 ml, 23 mmol) in MeOH (100 ml) was hydrogenated at 20 psi on a Parr® apparatus for 5 hours. The catalyst was removed by filtration and the filtrate evaporated in vacuo to give the desired piperidine as white solid (7.1 g, quant). $^1$H NMR (400 MHz, $CD_3OD$) δ: 1.58-1.72 (1H, m), 1.75-1.85 (1H, m), 2.08 (1H, d, J 14.2), 2.19 (1H, t, J 14.2), 2.28-2.38 (1H, m), 2.45 (2H, d, J 6.9), 3.24-3.32 (1H, m), 3.51-3.57 (1H, m), 3.67 (3H, s), 4.46 (1H, d, J 10.2), 7.72 (2H, d, J 8.3), 7.79 (2H, d, J 8.4).

The free base was obtained by treatment with $NaHCO_3$ (aq) and extraction in to DCM. The organic extracts were dried, filtered and evaporated.

Intermediate 2

(+)-Methyl {(2S,4R)-2-[4-(trifluoromethyl)phenyl]piperidin-4-yl}acetate

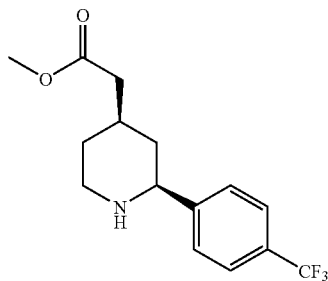

(±)-cis Methyl 4-(trifluoromethyl)phenylpiperidin-4-yl) acetate (Intermediate 1 [free base], 32.6 g, 0.108 mol), was dissolved in hot isopropanol (100 ml) and the solution was added to a solution of L-(+)-mandelic acid (9 g, 0.054 mol) in hot isopropanol (170 ml) and the resulting solution was allowed to stand at room temperature overnight. A white crystalline solid was deposited (17.55 g, 36%) and was filtered. The mother liquors were evaporated and the residue was neutralized with sodium carbonate (2M, 100 ml) and extracted with dichloromethane (3×100 ml). The combined extracts were washed with brine, dried (MgSO$_4$), filtered and evaporated. This extract was dissolved in hot isopropanol (100 ml) and was added to a solution of D-(−)-mandelic acid (9 g, 0.054 mol) in hot isopropanol (170 ml); immediate crystallization occurred and the mixture was allowed to stand for 2 h. The white crystalline solid was isolated by filtration (21 g, 44%) and was recrystallised from isopropyl acetate (250 ml) to give the product (19.8 g, 40%) as a white crystalline material, ee >99.5%. This material was neutralized with sodium carbonate (2M, 100 ml and extracted with dichloromethane (3×100 ml). The combined extracts were washed with brine, dried (MgSO$_4$), filtered and evaporated to give the free base: α$_D$ (c=1, MeOH) +23°; $^1$H NMR (360 MHz, CDCl$_3$) δ: 1.23 (6H, d, J 6.9), 2.88 (1H, qn, J 6.9), 4.27 (2H, s), 7.15-7.21 (4H, m), 7.71 (2H, d, J 8.2), 8.10 (2H, d, J 8.2).

Intermediate 3

(±)-Methyl {(2R*,4S*)-1-[(1S*)-1-(4-iodophenyl)-4-methylpentyl]-2-[4-(trifluoromethyl)phenyl]piperidin-4-yl}acetate

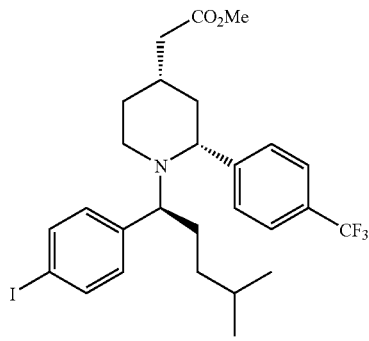

A mixture of equimolar amounts of Intermediate 1,4-iodobenzaldehyde and benzotriazole in toluene was stirred and heated at reflux under N$_2$ with a Dean-Stark trap for 18 hrs. After cooling to RT the solvent was removed in vacuo to give a thick oil which was used without further purification. 1-Bromo-3-methylbutane (3 molar equivalents) was added to stirred suspension of activated magnesium (3 molar equivalents) in dry Et$_2$O under N$_2$ at such a rate as to keep the internal temperature at ~30° C. After 90 mins at RT the reaction was cooled in an ice bath and a solution of zinc chloride in diethyl ether (1.0M, 3 molar equivalents) was added such that the internal temperature was <10° C. The cooling bath was removed and the reaction was stirred at RT for 1 hr, then recooled in an ice bath. A solution of the benzotriazole adduct (from above) in dry DCM was added via cannula such that the internal temperature <10° C. After 45 min at this temperature, the cooling bath was removed and the mixture was stirred at RT for 18 hrs. The reaction was cooled in an ice bath and quenched with saturated aqueous NH$_4$Cl. The mixture was diluted with DCM and H$_2$O, then filtered through Hyflo®. The layers were separated and the aqueous layer was extracted with DCM (×3). The combined extracts were dried (Na$_2$SO$_4$), filtered and evaporated. The residue was purified by chromatography (silica, 3-6% Et$_2$O/isohexane) to give the title compound in 65% yield. $^1$H NMR (400 MHz, CDCl$_3$) δ (ppm) 0.58-0.69 (1H, m), 0.81-0.83 (6H, m), 0.85-0.96 (1H, m), 1.13 (1H, dq, J 4.5, 12.8), 1.32 (1H, q, J 12.4), 1.42 (1H, septet, J 6.6), 1.63 (1H, br, d, J 13.2), 1.69-1.76 (2H, m), 1.80 (1H, qd, J 2.9, 12.8), 1.87-1.98 (1H, m), 1.13-1.26 (2H, m), 2.33 (1H, dt, J 2.4, 11.9), 2.68 (1H, td, J 3.0, 11.4), 3.35 (1H, dd, J 4.12, 9.6), 3.62 (3H, s), 3.7 (1H, dd, J 2.6, 10.9), 6.99 (2H, d, J 8.3), 7.54 (2H, d, J 7.8), 7.59-7.63 (4H, m); M/Z (ES+) 588 (M+H).

Example 1

(±) {(2S*,4R*)-1-{(1R*)-4-methyl-1-[6-(trifluoromethyl)pyridin-3-yl]pent-4-en-2-yn-1-yl}-2-[4-(trifluoromethyl)phenyl]piperidin-4-yl}acetic acid

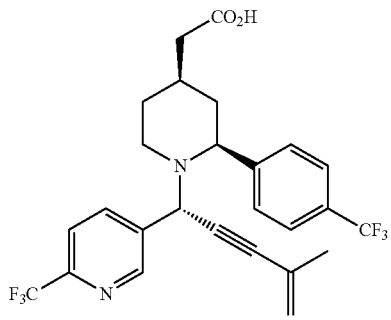

Step 1: 6-(Trifluoromethyl)nicotinaldehyde

A solution of [6-(trifluoromethyl)pyridine-3-yl]methanol (0.886 g, 5.0 mmol) in DCM (20 ml) was added to a mixture of Dess-Martin periodinane (2.334 g, 5.5 mmol) in DCM (20 ml) at rt. The reaction was stirred for 1.5 hrs then diluted with Et$_2$O (100 ml) and 4N NaOH (15 ml). The mixture was stirred for 10 mins then separated. The organic layer was washed with 4N NaOH (15 ml) then brine, dried (MgSO$_4$), filtered and evaporated. The residue was purified by chromatography (silica, 15% EtOAc/hexanes) to give the aldehyde (0.392 g, 45%). ¹HNMR (400 MHz, CDCl₃): δ 7.89 (1H, d, J 8.1), 8.37 (1H, d, J 8.1), 9.20 (1H, s), 10.22 (1H, s).

Step 2: (±) Methyl {(2S*,4R*)-1-{(1R*)-4-methyl-1-[6-(trifluoromethyl)pyridin-3-yl]pent-4-en-2-yn-1-yl}-2-[4-(trifluoromethyl)phenyl]piperidin-4-yl}acetate

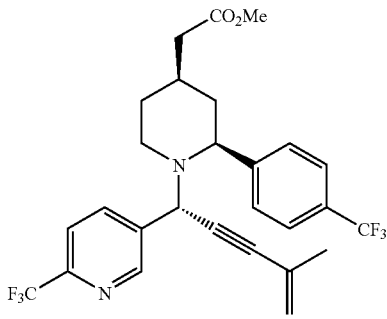

A mixture of the aldehyde from Step 1 (0.422 g, 2.4 mmol), Intermediate 1 (0.242 g, 0.8 mmol), 2-methyl-1-buten-3-yne (0.22 ml, 2.4 mmol) and AuBr₃ (35 mg, 0.08 mmol) in water (0.8 ml) was heated at 70° C. in the microwave for 1 hr. The reaction mixture was loaded onto an SCX cartridge and the crude product was eluted with 2N NH₃ in MeOH. The eluent was concentrated, diluted with EtOAc, washed with brine, dried (MgSO₄), filtered and evaporated. The residue was purified by chromatography (silica, 5-10% EtOAc/hexanes) to give the ester (0.270 g, 64%). ¹H NMR (400 MHz, CDCl₃): δ 1.26-1.32 (1H, m), 1.44 (1H, q, J 12.2), 1.73 (1H, m), 1.92 (1H, dq, J 13.0, 2.9), 2.00-2.04 (4H, m), 2.20-2.32 (2H, m), 2.44-2.54 (2H, m), 3.64 (3H, s), 3.69 (1H, dd, J 2.8, 11.3), 4.65 (1H, s), 5.34 (1H, brs), 5.42 (1H, s), 7.63 (5H, m), 7.98 (1H, m), 8.89 (1H, s).

Step 3: (±) {(2S*,4R*)-1-{(1R*)-4-methyl-1-[6-(trifluoromethyl)pyridin-3-yl]pent-4-en-2-yn-1-yl}-2-[4-(trifluoromethyl)phenyl]piperidin-4-yl}acetic acid A solution of the ester from Step 2 (0.146 g, 0.28 mmol) and LiOH (0.133 g, 5.6 mmol) in THF (3 ml) and water (3 ml) was stirred at rt for 16 hrs. The reaction mixture was acidified to pH6 with 2N HCl and extracted with EtOAc. The combined extracts were washed with brine, dried (MgSO₄), filtered and evaporated. The residue was purified by chromatography (silica, 1-2% MeOH/DCM) to give the acid (0.101 g, 71%). ¹H NMR (360 MHz, CD₃OD): δ 1.26-1.38 (1H, m), 1.51 (1H, q, J 12.1), 1.77 (1H, m), 1.90-1.98 (2H, m), 2.03 (3H, s), 2.24 (2H, d, J 6.9), 2.43-2.57 (2H, m), 3.74 (1H, dd, J 2.6, 11.4), 4.70 (1H, s), 5.39 (1H, m), 5.46 (1H, s), 7.70-7.72 (4H, m), 7.80 (1H, d, J 8.2), 8.17 (1H, d, J 8.1), 8.82 (1H, s).

Examples 2-20

The following compounds were made by the procedures in Example 1, using Intermediate 2 (Examples 2-16) or Intermediate 1 (Examples 17-19) and the appropriate aldehyde.

| Example | Structure | Name | M/Z ES⁺ [MH]⁺ |
|---|---|---|---|
| 2 | 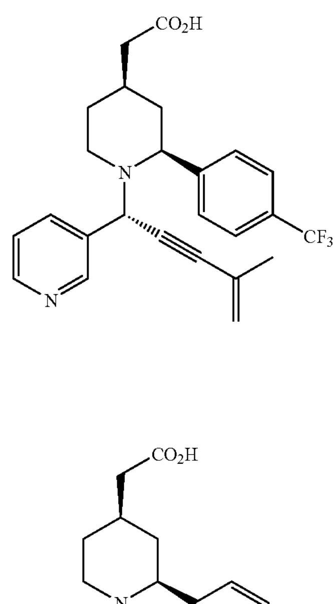 | {(2S,4R)-1-((1R)-4-methyl-1-pyridin-3-ylpent-4-en-2-yn-1-yl)-2-[4-(trifluoromethyl)phenyl]piperidine-4-yl} acetic acid | 443 |
| 3 | 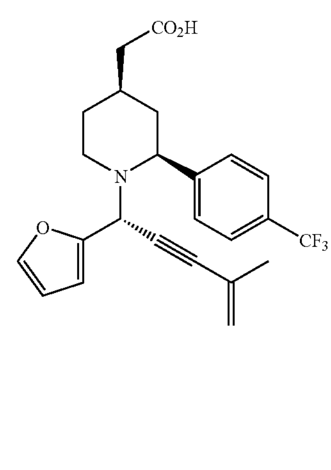 | {(2S,4R)-1-((1R)-1-furan-2-yl-4-methylpent-4-en-2-yn-1-yl)-2-[4-(trifluoromethyl)phenyl]piperidine-4-yl} acetic acid | 432 |

| Example | Structure | Name | M/Z ES+ [MH]+ |
|---|---|---|---|
| 4 | 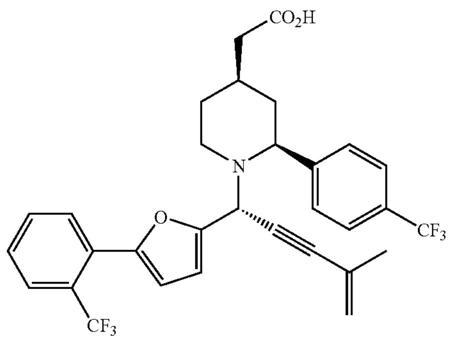 | {(2S,4R)-1-((1R)-4-methyl-1-{5-[2-(trifluoromethyl)phenyl]-furan-2-yl}pent-4-en-2-yn-1-yl)-2-[4-(trifluoromethyl)phenyl]piperidine-4-yl} acetic acid | 576 |
| 5 | 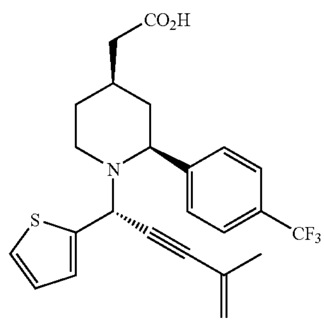 | {(2S,4R)-1-[(1R)-4-methyl-1-(2-thienyl)pent-4-en-2-yn-1-yl]-2-[4-(trifluoromethyl)phenyl]piperidine-4-yl} acetic acid | 448 |
| 6 | 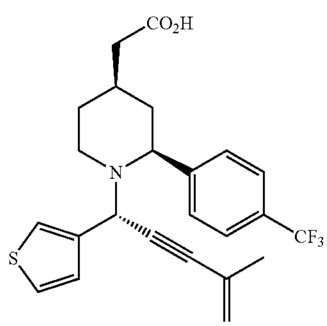 | {(2S,4R)-1-[(1R)-4-methyl-1-(3-thienyl)pent-4-en-2-yn-1-yl]-2-[4-(trifluoromethyl)phenyl]piperidine-4-yl} acetic acid | 448 |
| 7 | 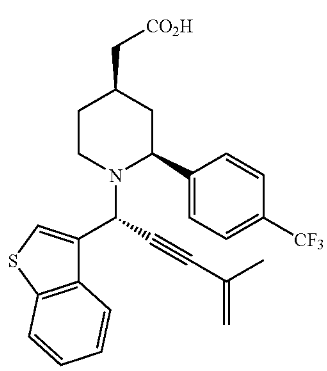 | {(2S,4R)-1-[(1R)-1-(1-benzothien-3-yl)-4-methylpent-4-en-2-yn-1-yl]-2-[4-(trifluoromethyl)phenyl]piperidine-4-yl} acetic acid | 498 |

-continued

| Example | Structure | Name | M/Z ES+ [MH]+ |
|---|---|---|---|
| 8 | 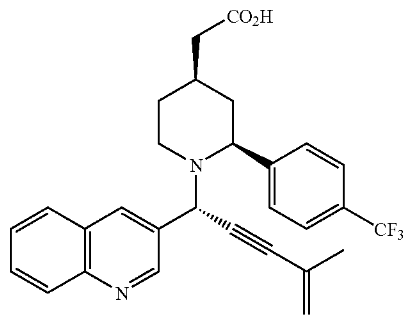 | {(2S,4R)-1-((1R)-4-methyl-1-quinolin-3-ylpent-4-en-2-yn-1-yl)-2-[4-(trifluoromethyl) phenyl] piperidine-4-yl} acetic acid | 493 |
| 9 | 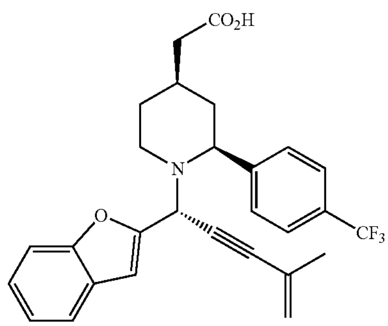 | {(2S,4R)-1-[(1R)-1-(1-benzofuran-2-yl)-4-methylpent-4-en-2-yn-1-yl]-2-[4-(trifluoromethyl) phenyl] piperidine-4-yl} acetic acid | 482 |
| 10 | 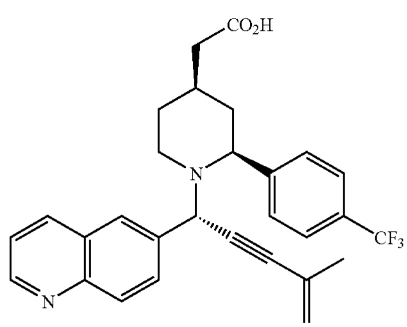 | {(2S,4R)-1-((1S)-4-methyl-1-quinoline-6-ylpent-4-en-2-yn-1-yl)-2-[4-(trifluoromethyl) phenyl]piperidine-4-yl} acetic acid | 493 |
| 11 | 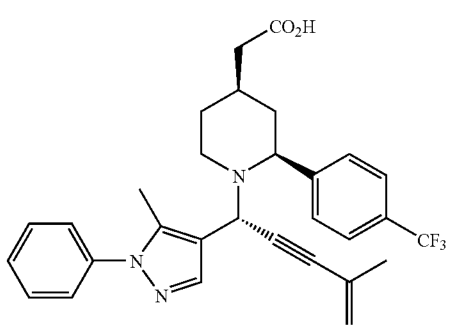 | {(2S,4R)-1-[(1R)-4-methyl-1-(1-phenyl-5-methyl-1H-pyrazol-4yl]pent-4-en-2-yn-1-yl)-2-[4-(trifluoromethyl) phenyl]piperidine-4-yl} acetic acid | 522 |

-continued

| Example | Structure | Name | M/Z ES+ [MH]+ |
|---------|-----------|------|---------------|
| 12 | 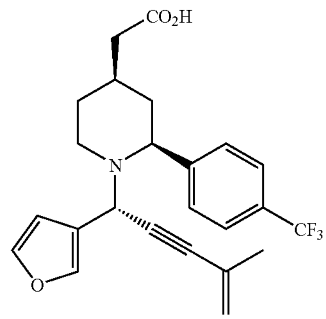 | {(2S,4R)-1-[(1R)-1-(3-furyl)-4-methylpent-4-en-2-yn-1-yl]-2-[4-(trifluoromethyl)phenyl]piperidine-4-yl} acetic acid | 432 |
| 13 | 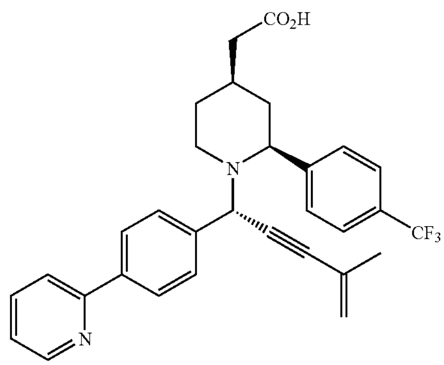 | {(2S,4R)-1-[(1S)-4-methyl-1-(4-pyridin-2-ylphenyl)pent-4-en-2-yn-1-yl]-2-[4-(trifluoromethyl)phenyl]piperidine-4-yl} acetic acid | 519 |
| 14 | 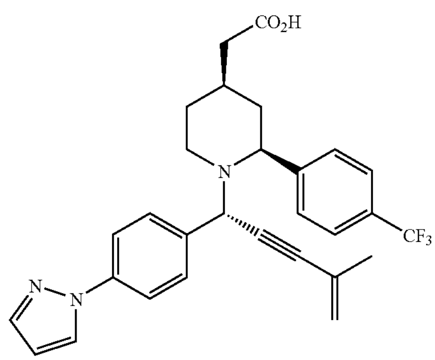 | {(2S,4R)-1-{(1S)-4-methyl-1-[4-(1H-pyrazol-1-yl)phenyl]pent-4-en-2-yn-1-yl}-2-[4-(trifluoromethyl)phenyl] piperidine-4-yl} acetic acid | 508 |
| 15 | 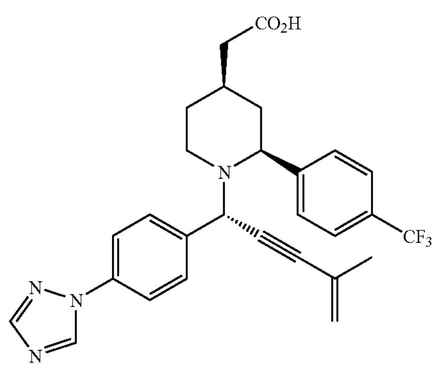 | {(2S,4R)-1-{(1S)-4-methyl-1-[4-(1H-1,2,4-triazol-1-yl)phenyl]pent-4-en-2-yn-1-yl}-2-[4-(trifluoromethyl)phenyl]piperidine-4-yl} acetic acid | 509 |

-continued

| Example | Structure | Name | M/Z ES+ [MH]+ |
|---|---|---|---|
| 16 | 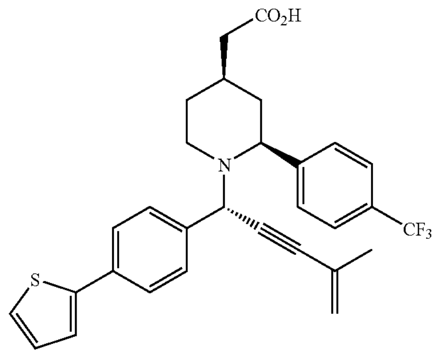 | {(2S,4R)-1-((1S)-4-methyl-1-{4-[2-thienyl]phenyl}pent-4-en-2-yn-1-yl)-2-[4-(trifluoromethyl) phenyl] piperidine-4-yl} acetic acid | 524 |
| 17 | 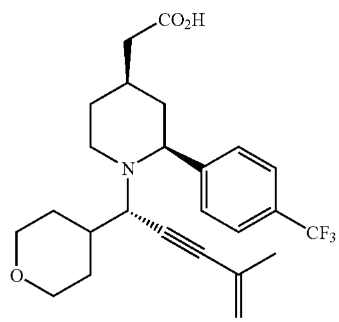 | (±) {(2S*,4R*)-1-[(1S*)-4-methyl-1-(tetrahydro-2H-pyran-4-yl)pent-4-en-2-yn-1-yl]-2-[4-(trifluoromethyl)phenyl] piperidin-4-yl} acetic acid | 450 |
| 18 | 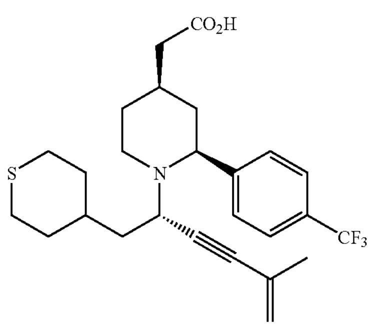 | (±) {(2S*,4R*)-1-[(1S*)-4-methyl-1-(tetrahydro-2H-thiopyran-4-ylmethyl)pent-4-en-2-yn-1-yl]-2-[4-(trifluoromethyl)phenyl] piperidin-4-yl}acetic acid | 480 |
| 19 | 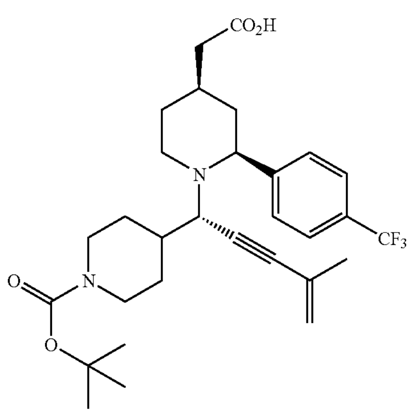 | (±) {(2S*,4R*)-1-{(1S*)-1-[1-(tert-butoxycarbonyl) piperidin-4-yl]-4-methylpent-4-en-2-yn-1-yl}-2-[4-(trifluoromethyl)phenyl] piperidin-4-yl} acetic acid | 549 |

| Example | Structure | Name | M/Z ES+ [MH]+ |
|---|---|---|---|
| 20 | 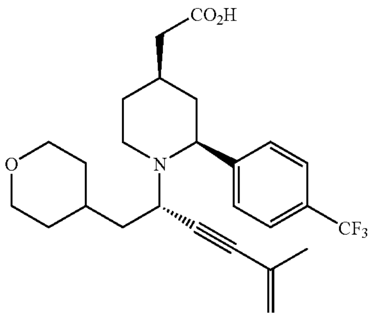 | {(2S,4R)-1-[(1S)-4-methyl-1-(tetrahydro-2H-pyran-4-ylmethyl)pent-4-en-2-yn-1-yl]-2-[4-(trifluoromethyl)phenyl]piperidin-4-yl} acetic acid | 464 |

Example 21

{(2S,4R)-1-[(1R)-4-methyl-1-(tetrahydro-2H-pyran-4-ylmethyl)pentyl]-2-[4-(trifluoromethyl)phenyl]piperidin-4-yl}acetic acid

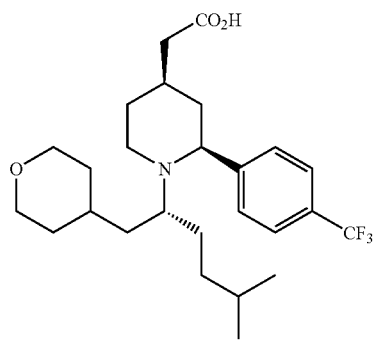

Step 1: Methyl {(2S,4R)-1-[(1R)-4-methyl-1-(tetrahydro-2H-pyran-4-ylmethyl)pentyl]-2-[4-(trifluoromethyl)phenyl]piperidin-4-yl}acetate

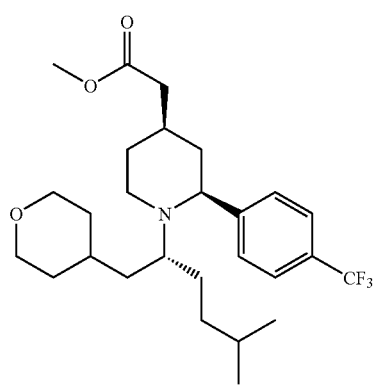

A solution of methyl {(2S,4R)-1-[(1S)-4-methyl-1-(tetrahydro-2H-pyran-4-ylmethyl)pent-4-en-2-yn-1-yl]-2-[4-(trifluoromethyl)phenyl]piperidin-4-yl}acetate (ester intermediate from the preparation of Example 20, 221 mg, 0.46 mmol) in MeOH (10 ml) was hydrogenated over Raney Nickel (500 mg) for 4 hrs at 45 psi. The catalyst was removed by filtration washing with $CH_2Cl_2$. The filtrate was evaporated and the residue was purified by chromatography (silica, 25% $Et_2O$/isohexane) to give the alkane (154 mg) as an oil. $^1$H NMR (360 MHz, $CDCl_3$): δ 0.62-0.70 (1H, m), 0.81-1.03 (10H, m), 1.08-1.95 (12H, m), 2.17-2.31 (4H, m), 2.95 (1H, brd, J 12.0), 3.33 (1H, t, J 11.6), 3.41 (1H, t, J 11.5), 3.58 (1H, d, J 9.0), 3.64 (3H, s), 3.86 (1H, brd, J 10.6), 3.92 (1H, brd, J 11.0), 7.38-7.40 (2H, d, m), 7.53 (2H, d, J 8.1); M/Z (ES+) 484 (MH+).

Step 2: {(2S,4R)-1-[(1R)-4-methyl-1-(tetrahydro-2H-pyran-4-ylmethyl)pentyl]-2-[4-(trifluoromethyl)phenyl]piperidin-4-yl}acetic acid

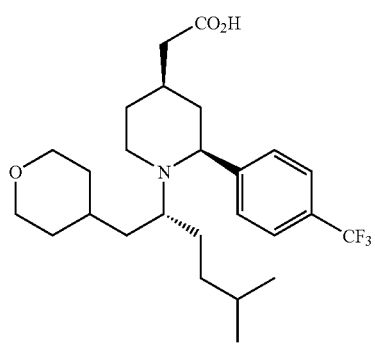

A solution of the methyl {(2S,4R)-1-[(1R)-4-methyl-1-(tetrahydro-2H-pyran-4-ylmethyl)pentyl]-2-[4-(trifluoromethyl)phenyl]piperidin-4-yl}acetate (Step 1, 142 mg, 0.29 mmol) and aqueous NaOH (4N, 220 μl, 0.88 mmol) in MeOH (2 ml) was heated at 60° C. for 3 hrs. After cooling to RT the MeOH was removed in vacuo, and the residue was partitioned between $CH_2Cl_2/H_2O$. 2N HCl (~0.5 ml) was added. The pH of the aqueous layer was adjusted to ~pH7 with saturated aqueous $NaHCO_3$. The aqueous layer was extracted with $CH_2Cl_2$ (×4). The combined extracts were dried ($Na_2SO_4$), filtered and evaporated. The residue was purified by chromatography (silica, 4-8% MeOH/$CH_2Cl_2$) to give the acid (113 mg) as a colourless solid. $^1$H NMR (360 MHz, $CD_3OD$): δ 0.65-0.75 (1H, m), 0.83-1.15 (11H, m), 1.18-1.55 (6H, m), 1.73-1.93 (5H, m), 2.18-2.30 (3H, m), 2.44 (1H, brt, J 12), 3.11 (1H, brd, J 12), 3.35 (1H, d, J 11), 3.43 (1H, d, J 12), 3.79 (2H, d, J 6.7), 3.88 (1H, d, J 8.0), 7.53 (2H, d, J 7.6), 7.63 (2H, d, J 8.2); M/Z (ES$^+$) 470 (MH$^+$).

Example 22

(±) {(2R*,4S*)-1-[(1S*)-4-methyl-1-(4-pyridin-4-ylphenyl)pentyl]-2-[4-(trifluoromethyl)phenyl]piperidin-4-yl}acetic acid

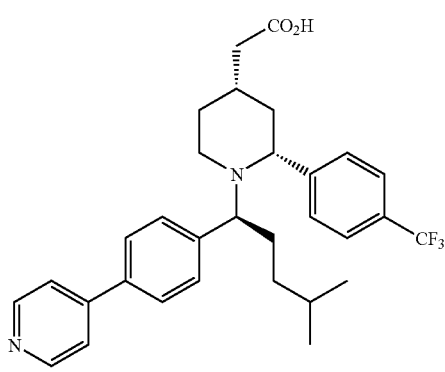

Step 1: (±) Methyl {(2R*,4S*)-1-[(1S*)-4-methyl-1-(4-pyridin-4-ylphenyl)pentyl]-2-[4-(trifluoromethyl)phenyl]piperidin-4-yl}acetate

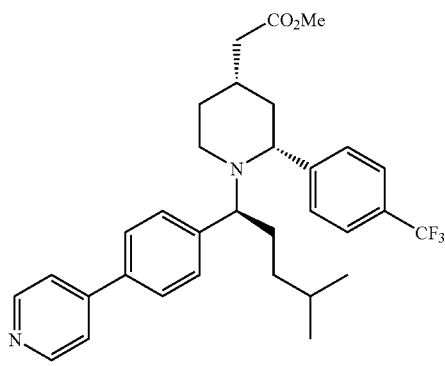

Intermediate 3 (130 mg, 0.22 mmol), pyridin-4-ylboronic acid (32 mg, 0.264 mmol), Pd(dppf)$_2$Cl$_2$ (9 mg, 0.011 mmol) and 2N aq. Na$_2$CO$_3$ in 1,4-dioxane (1 ml) were heated by microwave irradiation to 160° C. for 10 min. The reaction mixture was then diluted with MeOH, loaded onto a SCX cartridge, which was flushed with MeOH, then eluted with 2M NH$_3$ in MeOH. The NH$_3$ eluent was concentrated under reduced pressure to give the crude product which was purified by preparative reverse phase HPLC.

| Column | Column Dimensions | Percentage Modifier | Solvent | Mobile Phase | Flow | Detection |
|---|---|---|---|---|---|---|
| | 100 × 25 mm | 80-85% | MeCN | 0.1% TFA/water | 50 ml/min | MS (ES$^+$) |

The title compound was obtained as the TFA salt, 26 mg (18%). M/Z 539 (MH$^+$).

Step 2: (±) {(2R*,4S*)-1-[(1S*)-4-methyl-1-(4-pyridin-4-ylphenyl)pentyl]-2-[4-(trifluoromethyl)phenyl]piperidin-4-yl}acetic acid The product from Step 1 (26 mg, 0.048 mmol) was stirred in MeOH (1 ml) containing 6M aq. NaOH (0.05 ml) at RT for 18 h. The reaction mixture was concentrated under reduced pressure and the residue purified by preparative reverse phase HPLC.

| Column | Column Dimensions | Percentage Modifier | Solvent | Mobile Phase | Flow | Detection |
|---|---|---|---|---|---|---|
| Supelcosil ABZ + PLUS | 100 × 21.2 mm | 80-85% | MeCN | 0.1% aq. TFA | 15 ml/min | UV 230 nm |

The title compound was obtained as the TFA salt, 22 mg (72%). M/Z (ES+) 525. $^1$H NMR (500 MHz, CD$_3$OD): δ 0.64-0.72 (1H, m), 0.74-0.79 (1H, m), 0.85-0.87 (6H, m), 1.50 (1H, septet, J 6.6), 1.64 (1H, q, J 12.4), 1.95 (1H, q, J 12), 2.15-2.24 (3H, m), 2.28-2.41 (4H, m), 3.49 (1H, dt, J 2.5, 12.7), 3.72 (1H, d, J 12.1), 4.06 (1H, dd, J 2.5, 12.4), 4.96 (1H, dd, J 2.2, 11.5), 7.56 (2H, d, J 8.1), 7.88 (2H, d, J 7.1), 7.96 (2H, d, J 8.4), 8.02 (2H, d, 8.4), 8.25 (2H, d, J 5.9), 8.84 (2H, s).

Example 23

(±) {(2R*,4S*)-1-[(1S*)-4-methyl-1-(4-pyridin-3-ylphenyl)pentyl]-2-[4-(trifluoromethyl)phenyl]piperidin-4-yl}acetic acid

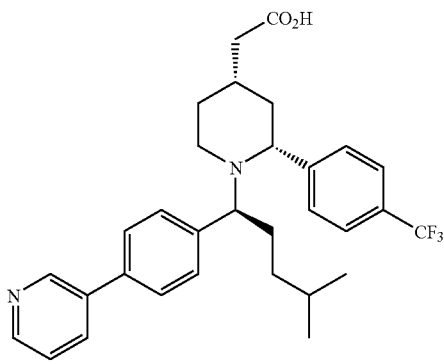

The title compound was prepared in an analogous manner to Example 22 using pyridine-3-ylboronic acid. M/Z (ES+) 525.

Example 24

(±) {(2R*,4S*)-1-[(1S*)-4-methyl-1-(4-pyridin-2-ylphenyl)pentyl]-2-[4-(trifluoromethyl)phenyl]piperidin-4-yl}acetic acid

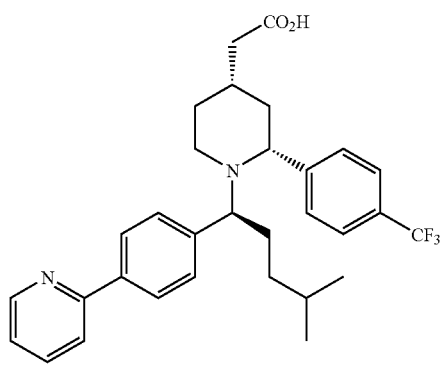

Step 1: (±) Methyl {(2R*,4S*)-1-[(1S*)-4-methyl-1-(4-pyridin-2-ylphenyl)pentyl]-2-[4-(trifluoromethyl)phenyl]piperidin-4-yl}acetate

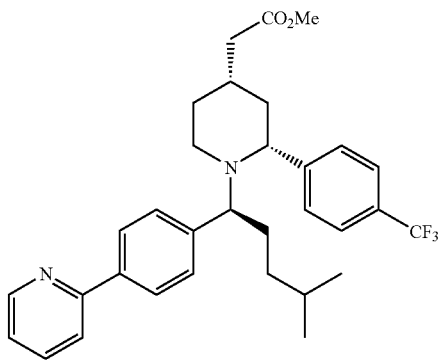

The iodobenzene precursor Intermediate 3 (587 mg, 1 mmol), 6-phenyl-2-pyridin-4-yl-1,2,6,2-dioxaazaborocane (536 mg, 2 mmol), tri-(o-tolyl)phosphine (61 mg, 0.2 mmol), Pd(OAc)$_2$ (11 mg, 0.05 mmol), K$_2$CO$_3$ (276 mg, 2 mmol) and CuI (76 mg, 0.4 mmol) in THF (3.5 ml) were heated by microwave irradiation to 150° C. for 20 min. The reaction mixture was diluted with MeOH and filtered through a pad of kieselgur filter aid. The filtrate was concentrated under reduced pressure and the residue purified by flash chromatography (silica gel, 5-40% EtOAc in iso-hexanes) to give the title compound, 200 mg (37%). M/Z (ES+) 539 (MH+).

Step 2: (±) {(2R*,4S*)-1-[(1S*)-4-methyl-1-(4-pyridin-2-ylphenyl)pentyl]-2-[4-(trifluoromethyl)phenyl]piperidin-4-yl}acetic acid The product from Step 1 (50 mg, 0.093 mmol) was hydrolysed in MeOH (1 ml) containing 6M aq. NaOH (0.1 ml, 0.6 mmol) at RT for 18 h. The solvent was removed under reduced pressure and the residue purified by preparative reverse phase HPLC:

| Column | Column Dimensions | Percentage Modifier | Solvent | Mobile Phase | Flow | Detection |
|---|---|---|---|---|---|---|
| Supelcosil ABZ + PLUS | 100 × 21.2 mm | 80-85% | MeCN | 0.1% aq. TFA | 15 ml/min | UV 230 nm |

The title compound was obtained as the bis-TFA salt, 35 mg (52%). M/Z (ES$^+$) 525 (MH$^+$). $^1$H NMR (500 MHz, CD$_3$OD): δ 0.65-0.72 (1H, m), 0.76-0.81 (1H, m), 0.83-0.85 (6H, m), 1.49 (1H, septet, J 6.5), 1.61 (1H, q, J 12.3), 1.93 (1H, q, J 12.4), 2.16-2.24 (3H, m), 2.27-2.40 (4H, m), 3.49 (1H, dd, J 2.8, 12.7), 3.75 (1H, d, J 12.7), 4.04 (1H, d, J 3.1, 13), 5.96 (1H, dd, J 2.7, 12.1), 7.48 (2H, d, J 8.4), 7.53-7.56 (1H, m), 7.85 (2H, d, J 7.8), 7.96-8.00 (3H, m), 8.07 (3H, d, J 8.1), 8.70 (1H, d, J 5.0). $^{19}$F NMR (470 MHz, CD$_3$OD): 8-64 (3F), −77 (6F).

Example 25 and 26

(±) {(2S,4R)-1-{(S)-(2R)-tetrahydrofuran-2-yl[4-(trifluoromethyl)phenyl]methyl}-2-[4-(trifluoromethyl)phenyl]piperidin-4-yl}acetic acid and (±) {(2S,4R)-1-{(S)-(2S)-tetrahydrofuran-2-yl[4-(trifluoromethyl)phenyl]methyl}-2-[4-(trifluoromethyl)phenyl]piperidin-4-yl}acetic acid

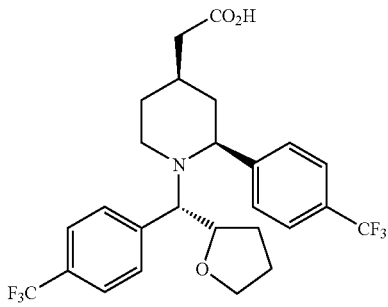

Step 1: (±) Methyl {(2S,4R)-1-{(S)-(2R)-tetrahydrofuran-2-yl[4-(trifluoromethyl)phenyl]methyl}-2-[4-(trifluoromethyl)phenyl]piperidin-4-yl}acetate and (±) methyl {(2S,4R)-1-{(S)-(2S)-tetrahydrofuran-2-yl[4-(trifluoromethyl)phenyl]methyl}-2-[4-(trifluoromethyl)phenyl]piperidin-4-yl}acetate

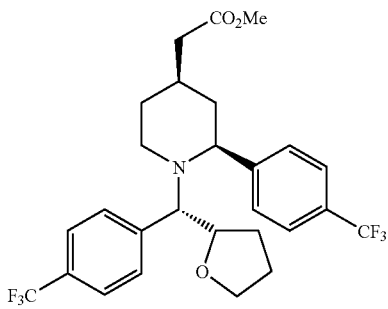

A solution of Intermediate 1 (3.0 g, 10 mmol), 4-(trifluoromethyl)benzaldehyde (1.37 ml, 10 mmol) and benzotriazole (1.19 g, 10 mmol) in toluene (50 ml) was heated at reflux under Dean & Stark conditions for 3 hours. The cooled reaction was evaporated in vacuo and the residue dissolved in DCM. A flask was charged with magnesium turnings (240 mg, 10 mmol) and dried under vacuum with stirring. Once at room temperature THF (5 ml) was added followed by 1-bromo-3,3,3-trifluoropropane (1066 µl, 10 mmol). The addition of a few drops followed by hand warming caused an exothermic reaction to initiate and the remaining bromide was added whilst maintaining the internal temperature at ~40° C. Once the addition was complete the mixture was stirred at room temperature for 30 minutes. The mixture was cooled to 0° C. and zinc chloride (suspension 1M in tBuOMe, 10 ml, 10 mmol) was added slowly maintaining the temperature below 0° C. during the addition, washed in with THF. Once the addition was complete the mixture was stirred at room temperature for 1 hour. The white suspension was cooled to 0° C. and the benzotriazole adduct (see above, 1.0 mmol) was added slowly as a solution in DCM (5 ml). The cooling was removed and air was allowed into the flask and the mixture was stirred at room temperature for 16 hours. The mixture was diluted with NH$_4$Cl (half sat) and with DCM and the mixture was filtered though a Celite® bed. The phases were separated and the aqueous layer was extracted with DCM. The extracts were dried (MgSO$_4$) and evaporated in vacuo to give a yellow gummy solid which was purified by flash chromatography (silica gel, 25-40-60-80% DCM in isohexane) to give the desired compound as two separate diastereoisomers.

Higher running diastereoisomer (87 mg, 16%) $^1$H (CDCl$_3$): δ 7.59 (2H, d, J 8.1), 7.50 (6H, t, J 9.1), 4.36-4.30 (1H, m), 3.85 (1H, d, J 8.6), 3.76-3.66 (2H, m), 3.62 (4H, d, J 4.6), 3.15 (1H, d, J 11.7), 2.72 (1H, t, J 11.0), 2.27-2.12 (2H, m), 1.98 (2H, dd, J 6.0, 10.5), 1.89-1.77 (3H, m), 1.70 (1H, d, J 12.3), 1.33-1.13 (3H, m). M/Z (ES$^+$) 530 (M+H).

Lower running diastereoisomer (43 mg, 8%). $^1$H NMR (CDCl$_3$): δ 7.64-7.49 (6H, m), 7.23 (2H, s), 4.70-4.64 (1H, m), 4.38 (1H, d, J 8.9), 3.78 (2H, t, J 6.4), 3.62 (4H, t, J 8.0), 3.49 (1H, t, J 8.5), 3.04 (1H, d, J 11.3), 2.82 (1H, t, J 10.7), 2.24-2.12 (3H, m), 2.01 (1H, s), 1.77-1.67 (4H, m), 1.29-1.15 (2H, m). M/Z (ES$^+$) 530 (M+H).

Step 2: (±) {(2S,4R)-1-{(S)-(2R)-tetrahydrofuran-2-yl[4-(trifluoromethyl)phenyl]methyl}-2-[4-(trifluoromethyl)phenyl]piperidin-4-yl}acetic acid and (±) {(2S,4R)-1-{(S)-(2S)-tetrahydrofuran-2-yl[4-(trifluoromethyl)phenyl]methyl}-2-[4-(trifluoromethyl)phenyl]piperidin-4-yl}acetic acid The title compound was prepared by hydrolysis of the higher running diastereoisomeric ester from Step 1 using the procedure described for Example 1 Step 3 to give a white foam (53 mg, 64%). $^1$H NMR (CD$_3$OD): δ 7.65-7.51 (8H, m), 4.45-4.39 (1H, m), 3.94 (1H, d, J 9.1), 3.69-3.61 (3H, m), 3.22 (1H, d, J 11.9), 2.79 (1H, t, J 11.2), 2.24-2.12 (2H, m), 2.05

(1H, d, J 6.3), 1.90-1.74 (4H, m), 1.54-1.44 (1H, m), 1.39-1.29 (2H, m), 1.25-1.17 (1H, m).

M/Z (ES$^+$) 516 (M+H).

The lower running diastereoisomeric ester from Step 1 was hydrolysed using the procedure described for Example 1 Step 3 to give a white foam after chromatography on silica eluting with 5% MeOH/DCM (7 mg, 18%). $^1$H NMR (CD$_3$OD): δ 7.72-7.56 (6H, m), 7.37 (2H, d, J 8.1), 4.79-4.73 (1H, m), 4.43 (1H, d, J 9.2), 3.86-3.78 (2H, m), 3.51 (1H, t, J 11.5), 3.14 (1H, d, J 11.4), 2.89 (1H, t, J 11.0), 2.22-2.12 (2H, m), 1.95 (1H, s), 1.76 (4H, t, J 12.3), 1.63 (1H, t, J 5.6), 1.35-1.25 (2H, m), 1.19 (1H, dd, J 8.8, 21.2), 1.03-0.97 (1H, m). M/Z (ES$^+$) 516 (M+H).

The invention claimed is:

1. A compound of formula I:

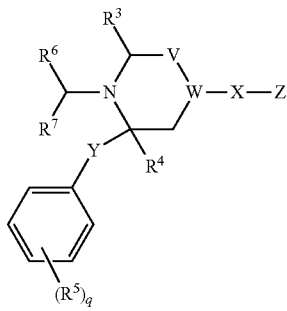

or a pharmaceutically acceptable salt thereof; wherein:
q is 0, 1, 2 or 3;
V represents a carbon atom whose remaining valencies are satisfied via bonding to H or X—Z or to any combination thereof;
W represents a carbon atom whose remaining valencies are satisfied via bonding to H or X—Z or to any combination thereof;
X represents a bond or C(R$^1$)$_2$ or CH$_2$C(R$^1$)$_2$;
Y represents a bond or CH$_2$ or CH$_2$CH$_2$;
Z represents CO$_2$H or a tetrazole ring;
each R$^1$ independently represents H or a non-aromatic hydrocarbon group of up to 6 carbon atoms; or the two R$^1$ groups complete a C$_{3-6}$alicyclic group;
R$^3$ and R$^4$ each represents H;
each R$^5$ independently represents halogen, C$_{1-6}$alkyl bearing 0-3 fluorine substituents, C$_{1-6}$alkoxy bearing 0-3 fluorine substituents, or C$_{2-6}$alkenyl; and
R$^6$ represents Het-A- where A represents a bond, CH$_2$ or 1,4-phenylene and Het represents a heterocyclic ring system of up to 10 ring atoms which optionally bears up to 3 substituents selected from halogen, C$_{1-4}$alkyl, CF$_3$, C$_{1-4}$alkoxy and C$_{1-4}$alkoxycarbonyl or which optionally bears a phenyl substituent which itself is optionally substituted with halogen, C$_{1-4}$alkyl, C$_{1-4}$alkoxy or C$_{1-4}$alkoxycarbonyl; and
R$^7$ represents a hydrocarbon group of up to 10 carbon atoms which optionally bears a CF$_3$ substituent.

2. A compound according to claim 1 or a pharmaceutically acceptable salt thereof wherein (R$^5$)$_q$ is selected from 2-CF$_3$, 3-CF$_3$, 4-CF$_3$, 2,4-di(CF$_3$), 2-F-4-CF$_3$, 4-OCF$_3$, 4-allyl, 4-n-propyl, 4-isopropyl and 4-tert-butyl.

3. A compound according to claim 1 of formula IV:

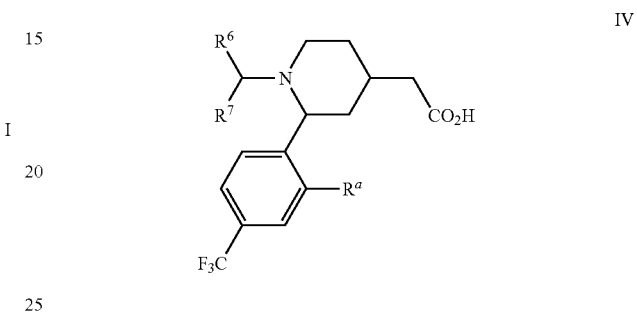

and the pharmaceutically acceptable salts thereof; wherein:
R$^a$ represents H, halogen or CF$_3$.

4. A compound according to claim 1 or claim 3 or a pharmaceutically acceptable salt thereof wherein R$^6$ is selected from 3-pyridyl, 6-trifluoromethyl-3-pyridyl, 2-furyl, 5-(2-trifluoromethylphenyl) -2-furyl, 2-thienyl, 3-thienyl, benzothiophen-3-yl, 3-quinolinyl, benzofuran-2-yl, 6-quinolinyl, 1-phenyl-5-methylpyrazol-4-yl, furan-3-yl, 4-(pyridin-2-yl)phenyl, 4-(pyrazol-1-yl)phenyl, 4-(1,2,4-triazol-1-yl) phenyl, 4-(thiophen-2-yl)phenyl, tetrahydropyran-4-yl, (tetrahydrothiopyran-4-yl)methyl, 1-(t-butoxycarbonyl)piperidin-4-yl, (tetrahydropyran-4-yl)methyl, 4-(pyridin-4-yl) phenyl, 4-(pyridin-3-yl)phenyl and tetrahydrofuran-2-yl.

5. A compound according to claim 1 or claim 3 or a pharmaceutically acceptable salt therof wherein R$^7$ is selected from methyl, ethyl, n-propyl, isopropyl, n-butyl, t-butyl, 3-methylbutyl, 2-ethylbutyl, 4-methylpentyl, 3,3-dimethylbutyl, 3-methylbuten-1-yl, 3-methylbut-3-en-1-ynyl, 4-methylpent-1-ynyl, 3,3-dimethylbut-1-ynyl, cyclohexyl, phenyl, cyclopropylmethyl, cyclohexylethynyl, benzyl, 2-phenylethyl, 2,2,2-trifluoroethyl, 3,3,3-trifluoropropyl, 4,4,4-trifluorobutyl, 1-methyl-3,3,3-trifluoropropyl, and 4-trifluoromethylphenyl.

6. A pharmaceutical composition comprising a compound according to claim 1 or a pharmaceutically acceptable salt thereof and a pharmaceutically acceptable carrier.

* * * * *